United States Patent [19]

Maass

[11] Patent Number: 4,817,595
[45] Date of Patent: Apr. 4, 1989

[54] VALVE FOR PRESSURE BANDAGE (FOR THE STAUNCHING OF A BLEEDING EXTERNAL WOUND)

[76] Inventor: Walter B. Maass, Hohenlohestrasse 26, 2800 Bremen, Fed. Rep. of Germany

[21] Appl. No.: 16,719
[22] PCT Filed: Mar. 24, 1986
[86] PCT No.: PCT/EP86/00176
   § 371 Date: Mar. 12, 1987
   § 102(e) Date: Mar. 12, 1987
[87] PCT Pub. No.: WO86/05385
   PCT Pub. Date: Sep. 25, 1986

[30] Foreign Application Priority Data

Mar. 23, 1985 [DE] Fed. Rep. of Germany ....... 3510667

[51] Int. Cl.$^4$ ............................................. A61F 13/00
[52] U.S. Cl. ........................... 128/155; 128/DIG. 20; 128/118.1
[58] Field of Search ....... 128/325, 326, 327, DIG. 20, 128/118, 129, 155, 156; 272/99; 137/855, 843, 856, 859

[56] References Cited

U.S. PATENT DOCUMENTS

| 2,045,750 | 6/1936 | Buschenfedt | 128/327 |
| 2,674,064 | 4/1954 | Gassaway | 137/846 X |
| 2,949,927 | 8/1960 | Mackal | 137/859 X |
| 3,171,410 | 3/1965 | Towle, Jr. et al. | 128/325 |
| 3,374,805 | 3/1968 | Trevarrow, Jr. | 137/843 |
| 3,460,168 | 8/1969 | BeBruyne | 137/855 |
| 3,766,924 | 10/1973 | Pidgeon | 128/325 |
| 3,874,387 | 4/1975 | Barbieri | 128/155 X |
| 4,224,945 | 9/1980 | Cohen | 128/155 X |
| 4,393,867 | 7/1983 | Baron | 128/87 R |
| 4,436,089 | 3/1984 | Schmid | 128/155 |

FOREIGN PATENT DOCUMENTS

| 2512689 | 10/1975 | Fed. Rep. of Germany | 137/855 |
| 48404 | 4/1984 | Japan | 137/855 |

Primary Examiner—Richard J. Apley
Assistant Examiner—Howard Flaxman
Attorney, Agent, or Firm—Wegner & Bretschneider

[57] ABSTRACT

The pressure bandage (1) for staunching a bleeding external wound (4) contains a hollow, gas-tight compress (2) which has at least one elastically ductile wall section (3), the outside of which can be laid against the wound to be treated. This wall section (3) is shaped toward the outsides through internal subjection to a fluid medium under pressure. For the generation of internal pressure the compress (2) is provided with a valve (11), the body (4') of which is made up of a flexible valve disk (6'). The latter is fixed to the wall of a fluid medium intake pipe (25) bordering on the flow cross section in such a way that when there is excess internal pressure in the compress (2) the valve disk is to be pressed with a sealing effect on the wall (9) which forms a valve seat (4') and which borders on the flow diameter. When excess pressure is exerted from the outside, the valve disk (6') is brought out of contact with the valve seat at at least one section of the latter's (4').

31 Claims, 3 Drawing Sheets

VALVE FOR PRESSURE BANDAGE (FOR THE STAUNCHING OF A BLEEDING EXTERNAL WOUND)

The invention relates to a pressure bandage for the staunching of a bleeding external wound, with a hollow gastight compress, having at least one elastically deformable wall section which is to be laid with its outside on the wound to be dressed and which is to be deformed outwardly by being acted upon from the inside by a flow medium under pressure above ambient pressure.

When speaking of a "pressure bandage" hereinabove or hereinbelow, this term should not be understood to mean exclusively a self-holding bandage whose compress is held on the patient's body by means of a gauze bandage, an adhesive plaster or the like. Rather, the pressure bandage according to the invention, as will be evident at once to the competent specialist, can be used in special cases even without special fastening means. Such a case may be present, for example, when dressing a root canal after extracting a tooth.

When speaking of a "compress" hereinabove or hereinbelow, this means an element with which a certain compression is to be exerted on a wound to be dressed, so as to prevent bleeding or to staunch bleeding that has already begun.

So-called compression or pressure bandages have long been known for the dressing of wounds. In this regard, reference is made only, for example, to German Pat. No. 188 337 or German Pat. No. 550 751. In these (pressure) "bandages" known for many decades, the compress is made of textile or textile-like material, e.g., gauze-enveloped wadding, absorbent gauze or the like.

Basically nothing has changed in these matters for many years. Thus, for example, in the 1965 DIN standard 13153 concerning "Fire wound bandage packs" it is written that this consists of a basket-weave staple-fiber fabric having a certain structure. A corresponding situation holds, for example, for the bandage compresses of the German Army (see the "Technical Delivery Conditions" TL 6510-002/3 of the Federal Office for Military Technology and Procurement, dated 1967).

Newer developments for pressure bandages (or at least bandages intended and suited as alternatives for them) also have as compress a blood-staunching pressure member which consists of a wound-up gauze bandage or the like (see, e.g., German patent application No. 28 40 667, applied for in 1978 and published in 1981). 6" represents the section of valve 6' in connection with annular valve seat 4'.

Although the compresses of the previously known pressure bandages that have been used millions of times to date have proved best in a large number of cases, there remains a neglected number of cases in which conventional pressure bandages fail or lead to some quite considerable difficulties. Such cases occur everyday in the professional area, e.g., in dental care, when, for example, a patient has had a tooth extracted, such patients not necessarily having to be among those having unusually low blood coagulation capacity (=bleeders or quasi-bleeders), but also in first-aid cases in which wounds generally first have to be provisionally dressed by laymen.

In the case of such after-bleeding from wounds (especially external ones) the treating physician has heretofore applied a so-called pressure tamponade, made of gauze or the like, and requested the affected patient, e.g., after extraction of a tooth, to press the upper and lower jaws tightly together for a certain (generally lengthy) time interval, so as to stop the bleeding. Apart from the fact that in many patients this can lead to variciform conditions in the jaw region in conjunction with a certain degree of psychic stress, this measure also frequently does not lead at all to the desired result, i.e., a quick staunching of bleeding from the affected wound.

A corresponding situation holds for many other medical cases, of which we shall cite as examples only the dressing of the chest after prior opening by means of a so-called imbricated bandage (recommended or prescribed by the DRK [German Red Cross]) or the dressing of an opened carotid artery, the last-cited case being especially critical not only because of the relatively large blood loss but also because the pressure above ambient pressure in the carotid artery creates a great danger of sucking in air from the surroundings, with the known consequences.

To prevent the difficulties occurring with conventional pressure bandages of the above-described type, there has been made known in DE-OS No. 31 45 110 an anatomic pressure bandage for stabilizing bone breaks and for controlling the bleeding from wounds, which has a flexible expandable shell containing at least two chemical reagents which when mixed form a gas with which an overpressure is to be generated during use in the compress consisting essentially of this shell. In use, the shell surrounds a body part (e.g., a wounded leg or a wounded arm), whereupon the chemical reagents are to be caused to mix by means of a manual action on the shell, so as in this manner to generate a gas which inflates the shell so as to exert a pressure on the body part to be dressed.

This known pressure bandage is already disadvantageous because, among other reasons, one of the reagents caused to react during use is located in capsules which are to be broken by action from the outside during use. As is known, this necessarily produces sharp edges which may cause a perforating of the compress, so that the latter is no longer usable.

In addition, in such a case the gas produced by the chemical reagents necessarily emerges from the compress and can reach the wound being dressed, which in many cases can be extremely disadvantageous. However, even when the use of this known pressure bandage does not cause a damaging of the compress, it is still extremely disadvantageous because the control provided for the internal pressure of the compress is highy deficient. Namely, if after breaking a capsule one ascertains that the internal pressure generated thereby in the compress is not high enough and one wants to break a second capsule (as is provided for in such a case with the known compress) in order to produce more gas by chemical reaction and thereby generate a higher internal pressure in the compress, another capsule cannot be found at all in the partially inflated condition of the compress. But even if one finds it, with the compress already expanded it is especially easy to damage it and make it unusable. Even if this should not happen, the pressure to be optimally set is only extremely poorly controllable, since a breaking of a second or even third capsule, if one can find it at all and can break it in the applied condition, does not raise the internal pressure continuously to the optimal point but rather stepwise, so that a too high pressure can very quickly come about. To be sure, in the embodiment of this known pressure bandage it is possible to actuate an outlet valve in such a case, but then—especially if such a pressure bandage is applied in a first-aid case by laymen or even the patient himself in a stress situation—there can very quickly be an excessive letting out of chemically produced gas, resulting in turn in a too slack condition of the compress, which, however, can then no longer be changed if the capsules present in the compress are used up.

Another disadvantage of these previously known pressure bandages is that they must be stored in an extremely careful manner while in stock and must not be subjected to any pressure, since in such a case—especially after a lengthy storage period—there may be an unintentional breaking of capsules and hence an inflation of the compress, e.g., in a bandage package or box, which not only makes the known pressure bandage unusable but also can cause extremely detrimental side effects when the bandage box is, for example, a bandage box carried in a motor vehicle, or when the bandage package is one carried by a soldier.

But even if it is assumed that this does not happen and that the chemical reagents in the interior of the compress do not become inactive during the storage period, it can still be noted as a drawback that these pressure bandages require a relatively large amount of space while in stock, that they must be stored protected from pressure, etc.

The present invention addresses the problem of improving the known pressure bandage of the above-described type, avoiding its aforesaid and other disadvantages, by the fact that it can be used, both in professional medical dressing and also in first-aid cases by laymen, in a reliable, simple and optimal manner for the treating of wounds with suitable control of the internal pressure of the compress producing the pressure on the wound being dressed; a possibly initially too low compress internal pressure is to be increased steadily without difficulty and a possibly too high compress pressure is to be reduced steadily in a simple manner, so that the pressure to be exerted on the wound being dressed can ultimately be made only as high or only somewhat higher than the pressure of the wounded blood vessels; furthermore, the pressure bandage according to the invention, especially in regard to its mass production required for first-aid applications, despite its advantages is to be produced as inexpensively as possible and is to be stored in an extremely space-saving manner while in stock; and it is to be ensured that no harmful effects are exerted by the pressure bandage on the wound being dressed.

To solve this problem it is provided according to the invention that the compress for generating the internal pressure above ambient pressure is provided with a valve whose valve body consists of a flexible valve disk which is fastened to the wall adjoining the flow cross-section in a flow-medium feed line for the compress in such a manner that when there is an internal excess in the compress it is to be pressed in a sealing manner against the wall which adjoins the flow cross-section and forms a valve seat, and that when there is an external excess at at least one section of the valve seat, i.e., when there is a pressure acting on the valve disk in the direction of the interior of the compress which is greater than the current internal pressure of the compress, as is the case, for example, during the inflation, it is to be brought out of contact with the valve seat, so that flow medium that is under an excess can flow from outside into the interior of the compress, or vice versa when an initially too high compress internal pressure is being adjusted to an optimal pressure value, i.e., from inside to outside, as will be explained in more detail hereinbelow.

The flexible valve disk is made preferably of a rubber-elastic material so as to achieve a good sealtightness, it being obvious that this effect can also be achieved if this valve seat is made of such a material, an especially good sealing action having been found with a version in which both the valve disk and the valve seat are rubber-elastically constructed, and especially if the valve seat is ring-shaped in accordance with a preferred embodiment of the present invention. This can be the case in a certain version of the present invention in which the end face facing toward the valve disk of a section of the flow-medium feed line or of a flange arranged thereon forms the valve seat.

According to the invention, an embodiment that can be produced extremely easily with maximum reliability and hence also correspondingly inexpensively, and which moreover is practically wear- and maintenance-free, consists in that the valve disk is connected in a gastight manner on a circumferential section of its outer edge section with the flow-medium feed line, which in the construction of the present invention can also be the case at several circumferential sections arranged with a spacing relative to one another, the valve disk or a circumferential section of the valve disk not connected to the flow-medium feed line preferably being (considerably) smaller than the circumferential section(s) connected in a gastight manner to the flow-medium feed line.

In order to have the valve of the pressure bandage according to the invention not act solely as a nonreturn valve but also to be usable in an advantageous manner as a control valve for the internal excess of the compress, the invention in a preferred embodiment further provides that the valve disk, in the region of an edge section not connected to the flow-medium feed line, is provided with a handle by means of which the edge section not connected to the flow-medium feed line can, also and especially when there is an internal excess of the compress, be brought out of contact with the valve seat, as is explained in detail hereinbelow, so that when the handle is actuated from the outside a possibly too high internal excess prevailing in the compress can be reduced by actuation of the handle. According to one embodiment of the present invention, such a handle can be an integral component of the valve disk, and in particular in such a version can be constructed as an extension, projecting outwardly over the flow-medium feed line and preferably extending through a through-hole in the flow-medium feed line, which in turn can be sealed off in a gastight manner to the outside by means of a rubber-elastic membrane or the like which preferably can be connected all around at its rim to the outside of the flow-medium feed line.

Especially when there is a relatively large flow cross-section with a relatively thin valve disk, which need not involve a "disk" in the ordinary sense—if, for example, it consists of an extremely thin foil section—in order to prevent the valve disk from being pressed or sucked practically through the valve seat due to the prevailing pressure conditions, in another embodiment of the present invention there can be provided on the side of the valve seat facing away from the valve disk a valve-disk support for which a wide variety of versions have proven very suitable.

Other preferred embodiments of the present invention are described in the subclaims.

The invention is further explained hereinbelow by exemplary embodiments with reference to a drawing in which FIG. 1 shows a diagrammatic basic illustration of the pressure bandage according to the invention with an elastically deformable wall section in a sectional illustration;

Figure 1:
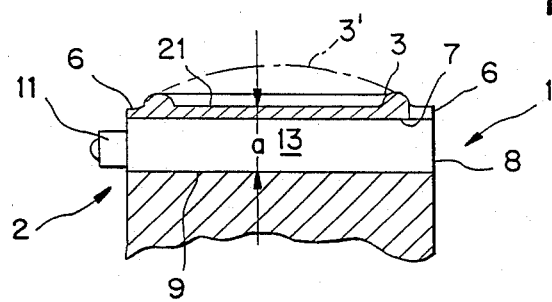

FIG. 1 of the drawing shows a diagrammatic illustration of a pressure bandage according to the invention, designated in its entirety by 1, for staunching a bleeding from an external wound. The pressure bandage 1 consists essentially of a compress 2 to be placed under pressure on a wound to be dressed. The compress 2 has a gastight construction, it has a wall section 3 which is to be laid with its outside on the wound 4 to be dressed (see FIG. 2) and which is to be deformed outwardly by being acted upon from the inside by a flow medium under excess.

Figure 2:
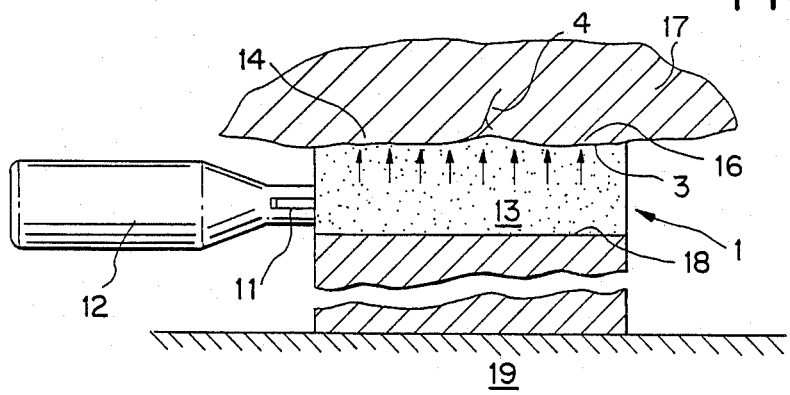
FIG. 2 shows a diagrammatic illustration of the pressure bandage per FIG. 1 in an application case.

In the exemplary embodiment according to FIGS. 1 and 2, the wall section 3, elastically deformable under internal excess, consists of a rubber compound and is cut from a web-shaped material, it being constructed in the manner of a membrane which is clamped with its rim 6 tightly—and indeed in a gastight manner—in the flange 7 of a frame 8. Between the elastically deformable wall section 3 and the opposite wall 9 of the compress 2 arranged at a distance a from it there is a valve 11 which (see FIG. 2) is to be connected to a (small) commercial $CO_2$ bottle 12 which serves as a (gas) pressurizer tank by means of which an overpressure compared to the ambient pressure (=atmospheric pressure) is to be generated in the chamber 13 between the elastic wall section 3 and the opposite wall 9. When the gas bottle 12 is connected to the the valve 11, the elastic wall section 3 bulges outward in the manner designated by a dot-dashed line 3' in FIG. 1.

FIG. 2 shows the pressure bandage 1 (with connected gas bottle 12) diagrammatically in use. The outside 14 of the elastic wall section 3 of the compress 2 is applied to the skin section 16 containing the wound 4 in question on the patient 17 in question, while the opposite outside 18 of the compress is braced by an "abutment" 19. This "abutment" 19 can be, for example, an ordinary (gauze) bandage, a (larger) adhesive plaster or also a part of the affected patient's body (e.g., his hand).

As soon as the outside 14 of the elastic wall section 3 is applied to the skin section 16 of the patient 17, and thus to the wound 4, the gas bottle 12 is connected to the nonreturn valve 11 so that there is a buildup of an overpressure in the chamber 13 and thus a exertion of by the elastic wall section 3 on the skin section 16 and thus on the wound 4.

It should be further pointed out that the outside 14 of the elastic wall section 3 facing toward the wound can be provided with a padding 21 of gauze and possibly wadding, so as to create a holding capacity for blood to be sucked up, as is a generally known feature of wound bandages.

Figure 3:
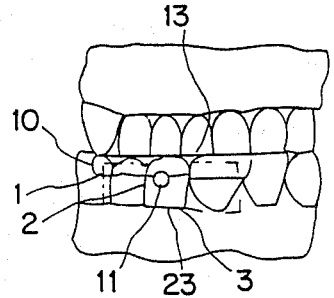
FIG. 3 shows a pillow-shaped version of the pressure bandage according to the invention with a totally elastically deformable compress.

FIG. 3 shows a variant of a pressure bandage 1 according to the invention in diagrammatic illustration. In this variant, the compress 2 has, at several surface sections not lying in one plane, wall sections which are outwardly deformable under flow-medium internal pressure, specifically both wall sections that run parallel to one another and also deformable surface sections which run at an angle to one another. For the compress 2 per FIG. 3 is essentially outwardly deformable over its entire surface under flow-medium internal pressure, i.e., has a practically pillow-shaped construction, and indeed approximately cubic in its middle section, with the end sections adjoining the middle section, illustrated by dot-dashed lines in FIG. 3, being widened so that the compress 2 is held positively in a tooth gap. Serving as abutment 19 is the cap 10 which is to be set onto the compress 2 from above and can be formed as a section of an impression tray. The compress 2 is made of a rubber-type foil material which is provided on its one side face with a valve 11, but could also be arranged in a flow-medium feed line as is generally the case (see, e.g., line 25 in FIGS. 6 to 11).

The pressure bandage 1 per FIG. 3 is used to dress a wound of a tooth root canal after successful extraction of a tooth, for purposes of blood staunching. Immediately after successful extraction and cleaning of the wound, the compress 2 is brought into the tooth gap and covered with a cap 10. Then the affected patient is asked to press the upper and lower jaws lightly together so as to hold the cap 10 in position. Then gas from a gas bottle 12 (not illustrated) to be connected to the nonreturn valve 11 is admitted into the chamber 13 of the compress 2, so that the compress 2 is outwardly deformed, it being braced on top against the cap 10 and against the side faces of the teeth located next to the tooth gap 23. The elastic wall section 3 facing toward the tooth gap 23 then presses against the wound in a sealing manner under the influence of the gas admitted under into the chamber 13 and has a surprisingly blood-staunching effect, so that after-bleeding usually ends after a short time.

Figure 4:
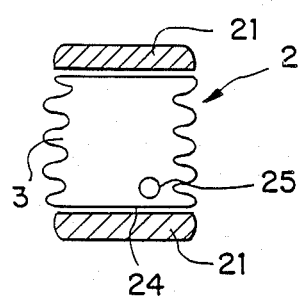
FIG. 4 shows a variant of the pressure bandage according to the invention in a bellow-shaped version with fixed but padded pressure plates.

FIG. 4 shows, also in diagrammatic illustration, a variant in which the deformable wall section 3 has a bellows-type construction. In such a version, the elastic wall section 3 does not act directly on the wound being dressed but rather acts in interaction with the flow-medium internal pressure more or less as a spring, while the head- and foot-side end plates 24 are fixed and are each provided with a pad 21, the pad 21 having a blood-staunching action on the wound being dressed under the pressure that is produced.

Figure 5:
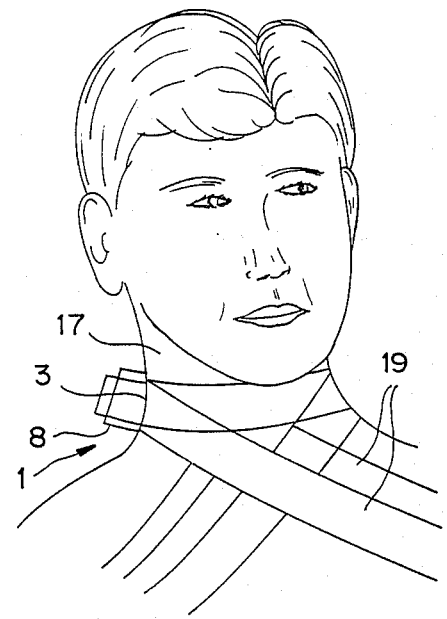
FIG. 5 shows another variant in diagrammatic illustration being used as a blood-staunching dressing of a carotid-artery injury.

FIG. 5 shows another variant of a pressure bandage 1 according to the invention with a frame 8 in which an elastic wall section 3 having the nature of a membrane is clamped in a gastight manner at the bottom (and possibly at the top). The "abutment" 19 for the pressure bandage 1 or the compress consists in the present—diagrammatically illustrated—case of a gauze bandage by means of which the pressure bandage 1 is fastened to the neck of the affected patient 17, so as to seal off his injured open artery and to prevent not only an excessive loss of blood but also a penetration of air into the carotid artery.

Figure 6:
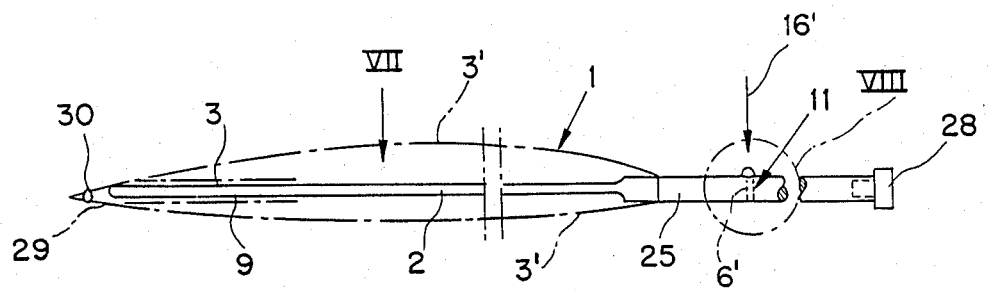
FIG. 6 shows a variant of the pressure bandage according to the invention, intended especially for first-aid purposes, in a side view indicated by the arrow VI in FIG. 7.
Figure 7:
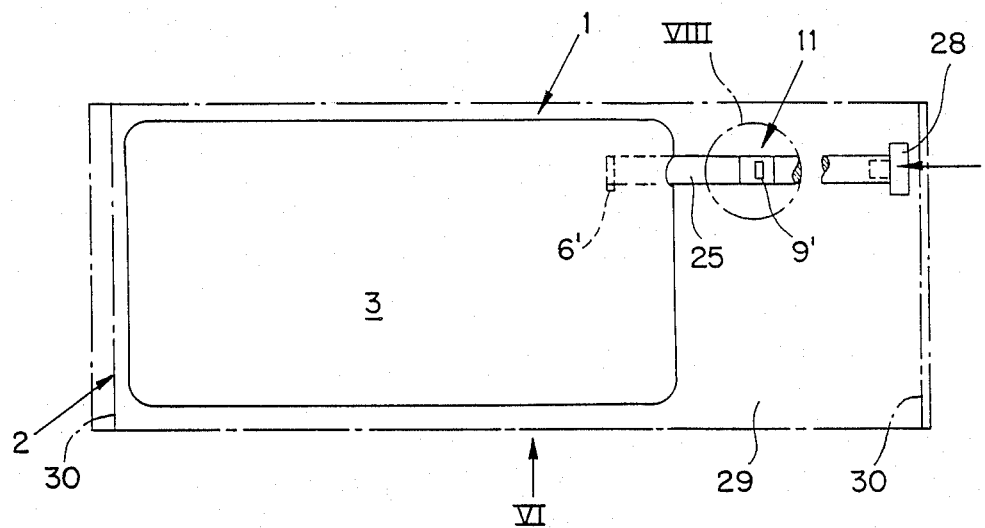
FIG. 7 shows a top view of the pressure bandage per FIG. 6 in the direction of the arrow VII in FIG. 6.

In the exemplary embodiment per FIGS. 6 and 7, intended and suited especially for first-aid purposes, the compress 2 is made entirely of a rubber compound and is cut from web-shaped material, so that the wall of the hollow-pillow-shaped compress 2 is constructed like a membrane. Between the upper wall section 3 and the thereunder-lying wall section 9 of the compress 2, a flow-medium feed line 25 containing a valve 11 opens out at one end laterally into the compress 2. The flow-medium feed line 25 consists of a rubber hose and is inflated at its free end section either with the mount or a small pump or possibly, if desired, with a small gas bottle in the applied state, after the compress 2 with its wall section 3 or 9 has been laid onto a wound to be dressed and has been fixed there, e.g., with a gauze bandage. Then there is produced in the chamber between the elastic wall sections 3 and 9 an pressure above ambient pressure (=atmospheric pressure), so that the elastic wall sections 3 and 9, insofar as they are not hindered by the gauze bandage, are bulged outwardly in the manner indicated by a dot-dashed line 3' in FIG. 6. Arranged [sic] with dot-dashed lines in FIG. 7 is a bag-shaped envelope 29 for the pressure bandage 1, which is sealed with a weld seam 30. Thus, the pressure bandage may be stored in a sterile envelope or other suitable sterile bandage package.

It should be further pointed out that in such a version the outside of the relevant elastic wall section 3 or 9 facing toward the wound can be provided with a padding made of gauze and/or wadding, as is the case in the version per FIG. 4 with respect to the pad 21, so as among other things to create a holding capacity for blood to be sucked up, as is a generally known feature of wound bandages.

Figure 8:
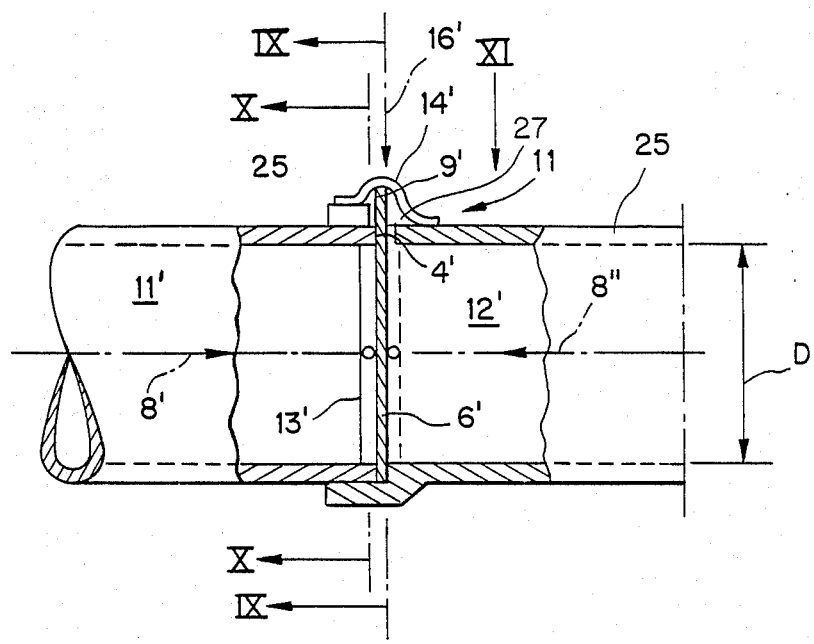
FIG. 8 shows an enlarged partial illustration of the section framed by a dot-dash circle in FIGS. 6 and 7 and designated by VIII, i.e, of the valve built into the flow-medium feed line.
Figure 9:
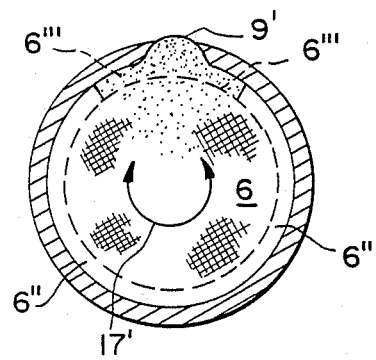
FIG. 9 shows a sectional illustration through the object of FIG. 8 seen in the direction of the section line IX—IX in FIG. 8.
Figure 10:
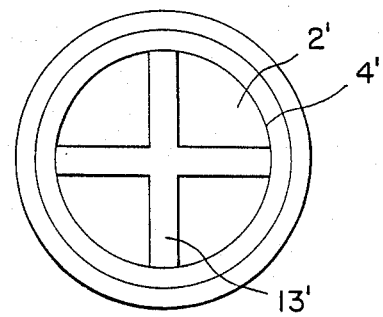
FIG. 10 shows a sectional illustration through the object of FIG. 8 seen in the direction of the section line X—X in FIG. VIII.
Figure 11:
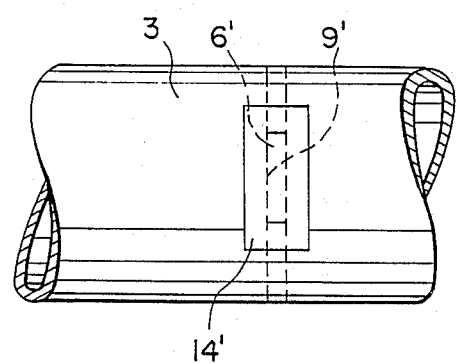
FIG. 11 shows a top view of the object of FIG. 8 seen in the direction of the arrow XI in FIG. 8.

FIGS. 8 to 10 show the valve, designated in its entirety by 11, by means of which the circular flow cross-section 2' of the line 25 (with diameter D) is to be either blocked or released. The flow cross-section 2' is bounded by the line 25, one of whose ends forms an annular valve seat 4' which possibly can be covered with a rubber-elastic material.

Associated with the valve seat 4' is a valve disk 6', acting as a valve body, which consists of a relatively thin flexible "membrane" made of a rubber-elastic material. The valve disk 6' is tightly glued over a central angle 17' of approximately 300° to a valve seat 4', i.e., the end face of the line 25, so that only a section 6''' is applied loosely on or to the valve seat 4'.

In a first operating position the valve 11 is closed [by] a flow-medium pressure directed onto the valve seat 4' in the direction of the arrow 8", since the valve disk 6' is pressed against the valve seat 4' with its rim section not tightly (gastight) connected to the end face (=valve seat 4') of the line 25, so that a flow-medium flow in this first flow direction 8" is prevented.

With inverse excess in the direction of the arrow 8', the effect is that the rim section of the valve disk 6' (which is provided with a handle 9' formed integrally on the valve disk 6') not tightly connected to the valve seat 4' is raised off the valve seat 4' and accordingly makes possible a corresponding flow-medium flow in the second flow direction 8', as is required for inflation. Over and above this nonreturn action, however, the valve 11 can also be opened in the first-cited operating position if the excess in the compress 2 is to be reduced. For this, one presses on the handle 9', whereby the valve disk 6' is raised off the valve seat 4', i.e., the valve 11 opens.

As can be seen from the drawing, the valve face of the valve seat 4' is circular, while the valve disk 6' is fashioned in the manner of a flat elastic flexible disk 6'.

To prevent the handle 9' from being pressed or sucked either into the chamber 11' lying to the left of the valve disk 6' in FIG. 8 or into the chamber 12' lying to the right of the valve disk 6' in FIG. 6 when the pressure difference across the valve is too high, there is provided a valve-disk support 13' which is constructed in the manner of a "cross hairs" (see FIG. 10), but which can also be Y-shaped, for example, or in some other manner in which it lets gas through and simultaneously provides support for the valve disk 6'. The valve-disc support also may be made of a mesh fabric running essentially parallel to the plane of the valve seat.

On the outside of the elastic flow-medium line 25, there is located at the sleeve-like connection point a slit-shaped passage 27 through which the handle 9', formed integrally with the valve disk 6', projects, so that it projects outwardly with a relatively small section over the line 25. The free end section of the handle 9' is glued in a gastight manner to a foil section 14'.

Despite its simple construction, freedom from maintenance, small number of parts moving relative to one another, flexible design, etc., the valve according to the invention meets the requirements that are to be imposed on such a valve and is relatively inexpensive to produce despite the solution it makes possible for diverse problems. Finally, it also proves especially well in the pressure bandage according to the invention because it cannot damage the compress material (especially if it is built into a flexible hose), cannot corrode, cannot break, etc., and because it in no way detrimentally impairs the sought extremely space-saving stockkeeping.

It should be further pointed out that the pressure bandage 1 according to the invention, using the valve 11 according to the invention, maintains its compress for an astonishingly long time. To still further delay any leakage losses (i.e., an unintentional pressure equalization), there can be inserted into the free end section of a flow-medium feed line 25 a plug-shaped closure 28 which, should reinflation become necessary, can be removed in an extremely easy manner and can be plugged back into the flow-medium feed line 25.

What is claimed is:

1. A pressure bandage for the staunching of bleeding external wounds, comprising:
   a hollow, gas-tight compress for covering the wound to be dressed, said compress having at least one elastically deformable wall section;

a fluid feed line for introducing a fluid into said compress to pressurize said compress;

a valve seat disposed in said fluid feed line; and a flexible valve disc having an outer edge provided with a first part connected to the valve seat and a second part capable of being moved into contact with and away from the valve seat, the valve disc being pressed in a circumferentially sealing manner against the valve seat when the internal pressure of the compress exceeds external pressure in the fluid feed line, the unconnected part of said valve disc being forced out of contact with the valve seat when external pressure in the fluid feed line exceeds the pressure in the compress, thereby permitting pressurizing of the interior of the compress, the unconnected edge section being provided with a handle whereby the unconnected edge section can be moved out of contact with the valve seat to relieve pressure within the compress.

2. Pressure bandage in accordance with claim 1, wherein said valve disk has a deformable elastic construction.

3. Pressure bandage in accordance with claim 1, wherein said valve seat has a deformable elastic construction.

4. Pressure bandage in accordance with claim 1, wherein said valve seat has an annular construction.

5. Pressure bandage in accordance with claim 1, wherein said valve seat is the end face of a section of the flow-medium feed line facing toward the valve disk.

6. Pressure bandage in accordance with claim 1, wherein said valve seat is a flange of the flow-medium feed line facing toward the valve disk.

7. Pressure bandage in accordance with claim 1, wherein said valve disk is connected in a gastight manner on several circumferential sections of its outer edge section with the valve seat.

8. Pressure bandage in accordance with claim 1, wherein said circumferential section of the valve disk not connected to the flow-medium feed line is smaller than the circumferential section connected in a gastight manner to the valve seat.

9. Pressure bandage in accordance with claim 1, wherein said handle is an integral component of the valve disk.

10. Pressure bandage in accordance with claim 9, wherein said handle is constructed as an extension projecting outwardly over the flow-medium feed line.

11. Pressure bandage in accordance with claim 10, wherein said handle extends through a through-hole of the flow-medium feed line.

12. Pressure bandage in accordance with claim 11, wherein said through-hole is sealed off in a gastight manner to the outside by a rubber-elastic foil section which is connected all around at its rim to the outside of the flow-medium feed line.

13. Pressure bandage in accordance with claim 1, wherein a valve-disk support is provided on the side of the valve seat facing away from the valve disk.

14. Pressure bandage in accordance with claim 13, wherein said valve-disk support consists of at least one extension of the flow-medium feed line.

15. Pressure bandage in accordance with claim 13, wherein said valve-disk support consists of at least one crosspiece running parallel to the plane of the valve seat.

16. Pressure bandage in accordance with claim 15, wherein said valve-disk support consists of at least two crosspieces running at an angle to each another.

17. Pressure bandage in accordance with claim 16, wherein two crosspieces run essentially at right angles to each other to form a valve-disk support.

18. Pressure bandage in accordance with claim 13, wherein said valve-disk support consists of a mesh fabric running essentially parallel to the plane of the valve seat.

19. Pressure bandage in accordance with claim 1, wherein said valve is connected to a gas bottle.

20. Pressure bandage in accordance with claim 1, wherein a closure capable of closing the flow-medium feed line in a gastight manner is placed at the end of the flow-medium feed line.

21. Pressure bandage in accordance with claim 1, wherein said compress is elastically deformable at at least two wall sections.

22. Pressure bandage in accordance with claim 21, wherein two elastically deformable wall sections of said compress are not in one plane.

23. Pressure bandage in accordance with claim 22, wherein said elastically deformable wall sections of said compress are essentially parallel to each other.

24. Pressure bandage in accordance with claim 22, wherein said elastically deformable wall sections of said compress are at an angle to each other.

25. Pressure bandage in accordance with claim 1, wherein said compress is made of an elastically deformable material.

26. Pressure bandage in accordance with claim 23, wherein said compress has a bellows-type construction, has a wall section essentially perpendicular to the bellows axis, is adapted to be laid with its outside on the wound to be dressed and has a fixed shape.

27. Pressure bandage in accordance with claim 26, wherein a fixed-shape compress section is provided with a pad on its outside facing toward the wound to be dressed.

28. Pressure bandage in accordance with claim 1, wherein a frame holds the deformable wall section(s) in a gastight manner.

29. Pressure bandage in accordance with claim 1, wherein a wall section of the compress facing toward a wound to be dressed has an essentially annular construction.

30. Pressure bandage in accordance with claim 1, capable of storage in a sterile envelope.

31. Pressure bandage in accordance with claim 1, capable of storage in a sterile bandage package.

* * * * *